(12) United States Patent
Heise et al.

(10) Patent No.: US 10,031,150 B2
(45) Date of Patent: Jul. 24, 2018

(54) LABORATORY SAMPLE DISTRIBUTION SYSTEM, LABORATORY SYSTEM AND METHOD OF OPERATING

(71) Applicant: Roche Diagnostics Operations, Inc., Indianapolis, IN (US)

(72) Inventors: Michael Heise, Marbach (DE); Hans Schneider, Schwaikheim (DE)

(73) Assignee: Roche Diagnostics Operations, Inc., Indianapolis, IN (US)

(*) Notice: Subject to any disclaimer, the term of this patent is extended or adjusted under 35 U.S.C. 154(b) by 0 days.

(21) Appl. No.: 15/380,443

(22) Filed: Dec. 15, 2016

(65) Prior Publication Data

US 2017/0097372 A1    Apr. 6, 2017

Related U.S. Application Data

(63) Continuation of application No. 14/920,097, filed on Oct. 22, 2015, now Pat. No. 9,575,086, which is a
(Continued)

(30) Foreign Application Priority Data

Nov. 4, 2011 (EP) ...................................... 11187982

(51) Int. Cl.
   *G01N 35/04*    (2006.01)
   *B65G 47/74*    (2006.01)
   (Continued)

(52) U.S. Cl.
   CPC .............. *G01N 35/04* (2013.01); *B65G 37/00* (2013.01); *B65G 54/02* (2013.01);
   (Continued)

(58) Field of Classification Search
   CPC ........ B65G 47/74; B65G 43/00; B65G 35/00; G01N 35/04; G01N 2035/046;
   (Continued)

(56) References Cited

U.S. PATENT DOCUMENTS 3,273,727 A    9/1966    Rogers et al.
3,653,485 A    4/1972    Donlon
(Continued)

FOREIGN PATENT DOCUMENTS

CN    201045617 Y    4/2008
CN    102109530 A    6/2011
(Continued)

*Primary Examiner* — Mark A Deuble
(74) *Attorney, Agent, or Firm* — Roche Diagnostics Operations, Inc.

(57) ABSTRACT

A laboratory sample distribution system is presented. The laboratory sample distribution system comprises a plurality of container carriers. The container carriers each comprise at least one magnetically active device such as, for example, at least one permanent magnet, and carry a sample container containing a sample. The system further comprises a transport plane to carry the multiple container carriers and a plurality of electro-magnetic actuators stationary arranged below the transport plane. The electro-magnetic actuators move a container carrier on top of the transport plane by applying a magnetic force to the container carrier. The system also comprises at least one transfer device to transfer a sample item, wherein the sample item is a container carrier, a sample container, part of the sample and/or the complete sample, between the transport plane and a laboratory station such as, for example, a pre-analytical, an analytical and/or a post-analytical station.

13 Claims, 6 Drawing Sheets

Related U.S. Application Data continuation of application No. 14/263,002, filed on Apr. 28, 2014, now Pat. No. 9,239,335, which is a continuation of application No. PCT/EP2012/071758, filed on Nov. 2, 2012.

(51) Int. Cl.
  *B65G 54/02* (2006.01)
  *B65G 37/00* (2006.01)

(52) U.S. Cl.
  CPC ............... *G01N 2035/0465* (2013.01); *G01N 2035/0477* (2013.01); *Y10T 436/114165* (2015.01)

(58) Field of Classification Search
  CPC ... G01N 2035/0474; G01N 2035/0475; G01N 2035/0489
  USPC ........ 198/339.1, 349, 465.1, 619; 422/63–67
  See application file for complete search history.

(56) References Cited

U.S. PATENT DOCUMENTS

| | | | |
|---|---|---|---|
| 3,901,656 A | 8/1975 | Durkos et al. |
| 4,150,666 A | 4/1979 | Brush |
| 4,395,164 A | 7/1983 | Beltrop et al. |
| 4,544,068 A | 10/1985 | Cohen |
| 4,771,237 A | 9/1988 | Daley |
| 5,120,506 A | 6/1992 | Saito et al. |
| 5,295,570 A | 3/1994 | Greckseh et al. |
| 5,309,049 A | 5/1994 | Kawada et al. |
| 5,523,131 A | 6/1996 | Isaacs et al. |
| 5,530,345 A | 6/1996 | Murari et al. |
| 5,636,548 A | 6/1997 | Dunn et al. |
| 5,641,054 A | 6/1997 | Mori et al. |
| 5,651,941 A | 7/1997 | Stark et al. |
| 5,720,377 A | 2/1998 | Lapeus et al. |
| 5,735,387 A | 4/1998 | Polaniec et al. |
| 5,788,929 A | 8/1998 | Nesti |
| 6,045,319 A | 4/2000 | Uchida et al. |
| 6,062,398 A | 5/2000 | Thalmayr |
| 6,141,602 A | 10/2000 | Igarashi et al. |
| 6,151,535 A | 11/2000 | Ehlers |
| 6,184,596 B1 | 2/2001 | Ohzeki |
| 6,191,507 B1 | 2/2001 | Peltier et al. |
| 6,206,176 B1 | 3/2001 | Blonigan et al. |
| 6,255,614 B1 | 7/2001 | Yamakawa et al. |
| 6,260,360 B1 | 7/2001 | Wheeler |
| 6,279,728 B1 | 8/2001 | Jung et al. |
| 6,293,750 B1 | 9/2001 | Cohen et al. |
| 6,429,016 B1 | 8/2002 | McNeil |
| 6,444,171 B1 | 9/2002 | Sakazume et al. |
| 6,571,934 B1 | 6/2003 | Thompson et al. |
| 7,028,831 B2 | 4/2006 | Veiner |
| 7,078,082 B2 | 7/2006 | Adams |
| 7,122,158 B2 | 10/2006 | Itoh |
| 7,278,532 B2 | 10/2007 | Martin |
| 7,326,565 B2 | 2/2008 | Yokoi et al. |
| 7,425,305 B2 | 9/2008 | Itoh |
| 7,428,957 B2 | 9/2008 | Schaefer |
| 7,578,383 B2 | 8/2009 | Itoh |
| 7,597,187 B2 | 10/2009 | Bausenwein et al. |
| 7,850,914 B2 | 12/2010 | Veiner et al. |
| 7,858,033 B2 | 12/2010 | Itoh |
| 7,875,254 B2 | 1/2011 | Garton et al. |
| 7,939,484 B1 | 5/2011 | Loeffler et al. |
| 8,240,460 B1 | 8/2012 | Bleau et al. |
| 8,281,888 B2 | 10/2012 | Bergmann |
| 8,502,422 B2 | 8/2013 | Lykkegaard |
| 8,796,186 B2 | 8/2014 | Shirazi |
| 9,097,691 B2 | 8/2015 | Onizawa et al. |
| 9,187,268 B2 | 11/2015 | Denninger et al. |
| 9,211,543 B2 | 12/2015 | Ohga et al. |
| 9,239,335 B2 | 1/2016 | Heise et al. |
| 9,423,410 B2 | 8/2016 | Buehr |
| 9,423,411 B2 | 8/2016 | Riether |
| 9,575,086 B2* | 2/2017 | Heise ............... B65G 54/02 |
| 2002/0009391 A1 | 1/2002 | Marquiss et al. |
| 2003/0092185 A1 | 5/2003 | Qureshi et al. |
| 2004/0050836 A1 | 3/2004 | Nesbitt et al. |
| 2004/0084531 A1 | 5/2004 | Itoh |
| 2005/0061622 A1 | 3/2005 | Martin |
| 2005/0109580 A1 | 5/2005 | Thompson |
| 2005/0194333 A1 | 9/2005 | Veiner et al. |
| 2005/0196320 A1 | 9/2005 | Veiner et al. |
| 2005/0226770 A1 | 10/2005 | Allen et al. |
| 2005/0242963 A1 | 11/2005 | Oldham et al. |
| 2005/0247790 A1 | 11/2005 | Itoh |
| 2005/0260101 A1 | 11/2005 | Nauck et al. |
| 2005/0271555 A1 | 12/2005 | Itoh |
| 2006/0000296 A1 | 1/2006 | Salter |
| 2006/0047303 A1 | 3/2006 | Ortiz et al. |
| 2006/0219524 A1 | 10/2006 | Kelly et al. |
| 2007/0116611 A1 | 5/2007 | DeMarco |
| 2007/0210090 A1 | 9/2007 | Sixt et al. |
| 2007/0248496 A1 | 10/2007 | Bondioli et al. |
| 2007/0276558 A1 | 11/2007 | Kim |
| 2008/0012511 A1 | 1/2008 | Ono |
| 2008/0029368 A1 | 2/2008 | Komori |
| 2008/0056328 A1 | 3/2008 | Rund et al. |
| 2008/0131961 A1 | 6/2008 | Crees et al. |
| 2009/0004732 A1 | 1/2009 | LaBarre et al. |
| 2009/0022625 A1 | 1/2009 | Lee et al. |
| 2009/0081771 A1 | 3/2009 | Breidford et al. |
| 2009/0128139 A1 | 5/2009 | Drenth et al. |
| 2009/0142844 A1 | 6/2009 | Le Comte |
| 2009/0180931 A1* | 7/2009 | Silbert ............... G01N 35/0099 422/63 |
| 2009/0322486 A1 | 12/2009 | Gerstel |
| 2010/0000250 A1 | 1/2010 | Sixt |
| 2010/0152895 A1 | 6/2010 | Dai |
| 2010/0175943 A1 | 7/2010 | Bergmann |
| 2010/0186618 A1 | 7/2010 | King et al. |
| 2010/0255529 A1 | 10/2010 | Cocola et al. |
| 2010/0300831 A1 | 12/2010 | Pedrazzini |
| 2010/0312379 A1 | 12/2010 | Pedrazzini |
| 2011/0050213 A1 | 3/2011 | Furukawa |
| 2011/0124038 A1* | 5/2011 | Bishop ............... C12Q 1/04 435/34 |
| 2011/0172128 A1 | 7/2011 | Davies et al. |
| 2011/0186406 A1 | 8/2011 | Kraus et al. |
| 2011/0287447 A1 | 11/2011 | Norderhaug et al. |
| 2012/0037696 A1 | 2/2012 | Lavi |
| 2012/0129673 A1 | 5/2012 | Fukugaki et al. |
| 2012/0178170 A1 | 7/2012 | Van Praet |
| 2012/0211645 A1 | 8/2012 | Tullo et al. |
| 2012/0275885 A1 | 11/2012 | Furrer et al. |
| 2012/0282683 A1 | 11/2012 | Mototsu |
| 2012/0295358 A1 | 11/2012 | Ariff et al. |
| 2012/0310401 A1 | 12/2012 | Shah |
| 2013/0034410 A1 | 2/2013 | Heise et al. |
| 2013/0126302 A1 | 5/2013 | Johns et al. |
| 2013/0153677 A1 | 6/2013 | Leen et al. |
| 2013/0180824 A1 | 7/2013 | Kleinikkink et al. |
| 2013/0263622 A1 | 10/2013 | Mullen et al. |
| 2013/0322992 A1 | 12/2013 | Pedrazzini |
| 2014/0170023 A1 | 6/2014 | Saito et al. |
| 2014/0234065 A1 | 8/2014 | Heise et al. |
| 2014/0234949 A1 | 8/2014 | Wasson et al. |
| 2015/0014125 A1 | 1/2015 | Hecht |
| 2015/0241457 A1 | 8/2015 | Miller |
| 2015/0273468 A1 | 10/2015 | Croquette et al. |
| 2015/0273691 A1 | 10/2015 | Pollack |
| 2015/0276775 A1 | 10/2015 | Mellars et al. |
| 2015/0276776 A1 | 10/2015 | Riether |
| 2015/0276777 A1 | 10/2015 | Riether et al. |
| 2015/0276778 A1 | 10/2015 | Riether et al. |
| 2015/0276781 A1 | 10/2015 | Riether et al. |
| 2015/0276782 A1 | 10/2015 | Riether |
| 2015/0360876 A1 | 12/2015 | Sinz |
| 2015/0360878 A1 | 12/2015 | Denninger et al. |
| 2016/0003859 A1 | 1/2016 | Wenczel et al. |
| 2016/0025756 A1 | 1/2016 | Pollack et al. |

(56) References Cited

U.S. PATENT DOCUMENTS

| | | |
|---|---|---|
| 2016/0054341 A1 | 2/2016 | Edelmann |
| 2016/0054344 A1 | 2/2016 | Heise et al. |
| 2016/0069715 A1 | 3/2016 | Sinz |
| 2016/0077120 A1 | 3/2016 | Riether |
| 2016/0097786 A1 | 4/2016 | Malinowski et al. |
| 2016/0229565 A1 | 8/2016 | Margner |
| 2016/0274137 A1 | 9/2016 | Baer |
| 2016/0282378 A1 | 9/2016 | Malinowski et al. |
| 2016/0341750 A1 | 11/2016 | Sinz et al. |
| 2016/0341751 A1 | 11/2016 | Huber et al. |
| 2017/0059599 A1 | 3/2017 | Riether |
| 2017/0096307 A1 | 4/2017 | Mahmudimanesh et al. |
| 2017/0101277 A1 | 4/2017 | Malinowski |
| 2017/0108522 A1 | 4/2017 | Baer |
| 2017/0131307 A1 | 5/2017 | Pedain |
| 2017/0131309 A1 | 5/2017 | Pedain |
| 2017/0131310 A1 | 5/2017 | Volz et al. |
| 2017/0138971 A1 | 5/2017 | Heise et al. |
| 2017/0160299 A1 | 6/2017 | Schneider et al. |
| 2017/0168079 A1 | 6/2017 | Sinz |
| 2017/0174448 A1 | 6/2017 | Sinz |
| 2017/0184622 A1 | 6/2017 | Sinz et al. |
| 2017/0248623 A1 | 8/2017 | Kaeppeli et al. |
| 2017/0248624 A1 | 8/2017 | Kaeppeli et al. |
| 2017/0363608 A1 | 12/2017 | Sinz |

FOREIGN PATENT DOCUMENTS

| | | |
|---|---|---|
| DE | 3909786 A1 | 9/1990 |
| DE | 102012000665 A1 | 8/2012 |
| DE | 102011090044 A1 | 7/2013 |
| EP | 0601213 A1 | 10/1992 |
| EP | 0775650 A1 | 5/1997 |
| EP | 0916406 A2 | 5/1999 |
| EP | 1122194 A1 | 8/2001 |
| EP | 1524525 A1 | 4/2005 |
| EP | 2119643 A1 | 11/2009 |
| EP | 2148117 A1 | 1/2010 |
| EP | 2327646 A1 | 6/2011 |
| EP | 2447701 A2 | 5/2012 |
| EP | 2500871 A1 | 9/2012 |
| EP | 2502675 B1 | 2/2014 |
| EP | 2887071 A1 | 6/2015 |
| GB | 2165515 A | 4/1986 |
| JP | S56-147209 A | 11/1981 |
| JP | 60-223481 A | 11/1985 |
| JP | 61-081323 A | 4/1986 |
| JP | S61-069604 A | 4/1986 |
| JP | S61-094925 A | 5/1986 |
| JP | S61-174031 A | 8/1986 |
| JP | S61-217434 A | 9/1986 |
| JP | S62-100161 A | 5/1987 |
| JP | S63-31918 A | 2/1988 |
| JP | S63-48169 A | 2/1988 |
| JP | S63-82433 U | 5/1988 |
| JP | S63-290101 A | 11/1988 |
| JP | 1148966 A | 6/1989 |
| JP | H01-266860 A | 10/1989 |
| JP | H02-87903 A | 3/1990 |
| JP | 03-112393 A | 5/1991 |
| JP | 03-192013 A | 8/1991 |
| JP | H03-38704 Y2 | 8/1991 |
| JP | H04-127063 A | 4/1992 |
| JP | H05-69350 A2 | 3/1993 |
| JP | H05-142232 A | 6/1993 |
| JP | H05-180847 A | 7/1993 |
| JP | 06-26808 A | 2/1994 |
| JP | H06-148198 A | 5/1994 |
| JP | 06-156730 A | 6/1994 |
| JP | 06-211306 A | 8/1994 |
| JP | 07228345 A | 8/1995 |
| JP | 07-236838 A | 9/1995 |
| JP | H07-301637 A | 11/1995 |
| JP | H09-17848 A | 1/1997 |
| JP | H11-083865 A | 3/1999 |
| JP | H11-264828 A | 9/1999 |
| JP | H11-304812 A | 11/1999 |
| JP | H11-326336 A | 11/1999 |
| JP | 2000-105243 A | 4/2000 |
| JP | 2000-105246 A | 4/2000 |
| JP | 2001-124786 A | 5/2001 |
| JP | 2001-240245 A | 9/2001 |
| JP | 2005-001055 A | 1/2005 |
| JP | 2005-249740 A | 9/2005 |
| JP | 2006-106008 A | 4/2006 |
| JP | 2007-309675 A | 11/2007 |
| JP | 2007-322289 A | 12/2007 |
| JP | 2007314262 A2 | 12/2007 |
| JP | 2009-036643 A | 2/2009 |
| JP | 2009-062188 A | 3/2009 |
| JP | 2009-145188 A | 7/2009 |
| JP | 2009-300402 A | 12/2009 |
| JP | 2010-243310 A | 10/2010 |
| JP | 2013-172009 A2 | 2/2013 |
| JP | 2013-190400 A | 9/2013 |
| SU | 685591 A1 | 9/1979 |
| WO | 96/36437 A1 | 11/1996 |
| WO | 03/042048 A3 | 5/2003 |
| WO | 2007/024540 A1 | 3/2007 |
| WO | 2008/133708 A1 | 11/2008 |
| WO | 2009/002358 A1 | 12/2008 |
| WO | 2010/042722 A1 | 4/2010 |
| WO | 2010/085670 A1 | 7/2010 |
| WO | 2012/170636 A1 | 7/2010 |
| WO | 2010/087303 A1 | 8/2010 |
| WO | 2010/129715 A1 | 11/2010 |
| WO | 2011/138448 A1 | 11/2011 |
| WO | 2012/158520 A1 | 11/2012 |
| WO | 2012/158541 A1 | 11/2012 |
| WO | 2013/152089 A1 | 10/2013 |
| WO | 2013/169778 A1 | 11/2013 |
| WO | 2013/177163 A1 | 11/2013 |
| WO | 2014/059134 A1 | 4/2014 |
| WO | 2014/071214 A1 | 5/2014 |

* cited by examiner

| | | | | | |
|---|---|---|---|---|---|
| t=0 | 5_1=OFF | 5_2=ON | 5_3=OFF | 5_4=OFF | 5_5=OFF |
| t=1 | 5_1=OFF | 5_2=OFF | 5_3=ON | 5_4=OFF | 5_5=OFF |
| t=2 | 5_1=OFF | 5_2=OFF | 5_3=OFF | 5_4=ON | 5_5=OFF |

Fig.9

| | | | |
|---|---|---|---|
| t=0 | 5_1=N | 5_2=OFF | 5_3=S |
| t=1 | 5_1=OFF | 5_2=S | 5_3=OFF |
| t=2 | 5_1=OFF | 5_2=OFF | 5_3=N |

Fig. 10

LABORATORY SAMPLE DISTRIBUTION SYSTEM, LABORATORY SYSTEM AND METHOD OF OPERATING

CROSS-REFERENCE TO RELATED APPLICATIONS

This application is a continuation of patent application Ser. No. 14/920,097, filed on Oct. 22, 2015, now allowed, which is a continuation of patent application Ser. No. 14/263,002, filed on Apr. 28, 2014, now U.S. Pat. No. 9,239,335, which is a continuation of PCT/EP2012/071758, filed Nov. 2, 2012, which is based on and claims priority to EP 11187982.1, filed Nov. 4, 2011, which are hereby incorporated by reference.

BACKGROUND

The present disclosure generally relates to a laboratory sample distribution system, a laboratory system and a corresponding method of operation.

Laboratory sample distribution systems are used to distribute samples or specimens, for example, blood, between various different laboratory stations or specimen-processing instruments, such as pre-analytical stations, analytical stations and post-analytical stations, of a laboratory system.

In one prior art system, a drive mechanism which operates to advance specimen-container racks on a surface by producing an X/Y movable magnetic field below the surface. The movable magnetic field is produced by permanent magnets carried by an X/Y movable magnetic truck assembly. The magnetic field produced by each magnet magnetically couples with magnetically-attractive members carried in a base portion of each specimen-transport rack. The magnetic bond between the magnets and magnetically-attractive members is sufficiently strong that, as the magnetic truck assembly moves in the X/Y plane, a magnetically-coupled rack follows. Due to mechanical constraints caused by the X/Y movable magnetic truck assembly independent simultaneous movements of multiple specimen-transport racks are difficult to implement. Further, specimen-containers can only be moved together in specimen-transport rack quantities.

Therefore, there is a need to provide a laboratory sample distribution system, a laboratory system and a method of operating that is highly flexible and offers a high transport performance.

SUMMARY

According to the present disclosure, a laboratory sample distribution system and method are presented. The laboratory sample distribution system can comprise a plurality of container carriers. Each container carrier can comprise at least one magnetically active device and can carry a sample container containing a sample. The system can further comprise a transport plane to carry the plurality of container carriers and a plurality of electro-magnetic actuators stationary arranged below the transport plane. The plurality of electro-magnetic actuators can move a container carrier on top of the transport plane by applying a magnetic force to the container carrier. The system can also comprise at least one transfer device to transfer a sample item between the transport plane and a laboratory station. The sample item can be a container carrier, a sample container, part of the sample and/or the complete sample.

Accordingly, it is a feature of the embodiments of the present disclosure to provide a laboratory sample distribution system, a laboratory system and a method of operating that is highly flexible and offers a high transport performance. Other features of the embodiments of the present disclosure will be apparent in light of the description of the disclosure embodied herein.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which.

DETAILED DESCRIPTION

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

A laboratory sample or specimen distribution system can comprise a plurality of container carriers such as, for example about 50 to about 500 container carriers. The container carriers cannot be self-powered. The container carriers can comprise at least one magnetically active, i.e. magnetically attractive, device and can carry a single sample container. Further, the system can comprise a two dimensional transport plane or supporting surface, which may be completely planar and can carry at least part of the container carriers. A plurality of electro-magnetic actuators such as, for example about 50 to about 5000 electro-magnetic actuators, can be arranged stationary or fixed below the transport plane. The electro-magnetic actuators can move a container carrier on top of the transport plane in at least two different directions by applying or causing a magnetic force to the container carrier, i.e. to the magnetically active device of the container carrier.

The transport plane can support the container carriers in a way to allow movement along directions as guided by magnetic forces. Accordingly, the transport plane can be continuous in at least those directions of movements to allow a smooth travel of the container carriers. In order to allow a flexible transfer of carriers along many lateral directions, a flat transport plane can be an advantage. On a microscopic level, it can be advantageous to employ a surface with many small protrusions in order to reduce friction between the transport plane and the bottom surface of the container carrier.

Further at least one, for example, automatic, transfer device can be provided to, for example, automatically, transfer or move a sample item between the transport plane and a laboratory station. The sample item can be a container carrier, a sample container, part of the sample and/or the complete sample. The term "automatic" can mean that the transfer can be performed using a process control or control device controlling the necessary devices used for the transfer. In the case of an automatic transfer, no human or manual interaction may be necessary for the transfer. The laboratory station may be a pre-analytical, an analytical and/or a post-analytical station as typically used in laboratory systems. An analytical station or analyzer, for example, may use the sample or part of the sample and a reagent to generate a measurable signal based on which the presence or concentration of the analyte can be determined.

The transfer device can provide an interface between the transport plane and the laboratory station. The transfer device can be arranged such that even conventional laboratory stations placed adjacent to the transport plane can easily interface with the transport plane without modification. The transfer device may, for example, comprise a picker for picking the container carrier or the sample container. The picker can move along predetermined axes such as, for example, along a vertical axis Z and along a single horizontal axis X or Y. If the laboratory station operates rack based, i.e. processes samples or sample containers provided in a sample container rack placed at specific positions, the transfer device may transfer the sample containers from the transport plane to the sample container rack and vice versa. The transfer device may also be incorporated as a pipettor. The pipettor may, for example, take part of the sample contained in a sample container and can transfer this sample to a laboratory station.

The transfer device may be provided separate from the transport plane and the laboratory station, i.e. the transport plane, the transfer device and the laboratory station may be provided as separate modules or devices. Alternatively, the transfer device may be part of the laboratory station.

The transfer device may provide a sample container rack formatting and/or reformatting operation. Formatting can mean that the transfer device can transfer the sample containers from the transport plane to one or more sample container racks. Reformatting can mean that the transfer device can transfer the sample containers from one or more sample container racks to container carriers on the transport plane.

Since a sample container can be carried by a corresponding individually movable container carrier, the sample containers may be moved over the transport plane with high flexibility. Together with the transfer device performing a formatting/reformatting operation, the laboratory station may operate rack based with optimized throughput.

The sample container racks may have different rack formats. The rack format can specify amongst others the number of sample containers which can be placed in the sample container rack, i.e. the container capacity.

A specific rack format may correspond to a specific laboratory station. The transfer device may adapt to a specific rack format. The transfer device may determine the rack format, for example, by suitable sensors. After having determined the rack format, the transfer device may perform the formatting/reformatting operation rack format specific, for example, by placing the corresponding number of sample containers into the sample container rack.

The sample containers may be delivered for processing comprised in input sample container racks which can be placed automatically by a corresponding device or manually at a specific location adjacent to a dedicated transfer device. This transfer device may take the sample containers from the input sample container rack and place it in corresponding empty container carriers, for example, provided in one or more buffer areas to store container carriers actually not carrying a sample container. After being processed, the sample containers may be transferred to a corresponding output sample container rack by a dedicated transfer device. The type of the input sample container rack and the type of the output sample container rack may differ.

The operation of the transfer devices, the operation of the transport plane and the operation of the laboratory stations may be synchronized as follows. One way to synchronize operations can be to provide data communications between the transport plane, the transfer devices and the laboratory station. The transport plane may signal to the transfer device that a container carrier can be placed at a specific transfer location. As a result, the transfer device may signal to the corresponding laboratory station that a sample container is ready for analysis. The laboratory station then may signal to the transfer device to transfer the sample container to the laboratory station if processing capacity is available.

The workflow for transferring sample containers from the transport plane to the laboratory stations may also be controlled by a master control device in data communication with the transport plane, the transfer devices and the laboratory stations. The data communication may be done according to a predetermined data communication protocol including software and hardware specification.

Additionally or alternatively, sensors may be provided to signal to the transfer device that a sample container is ready for transfer, for example, has reached a transfer location. Such a sensor may be an optical sensor or a magnet sensor such as, for example, a hall sensor, sensing a container carrier at a specific transfer location on the transport plane.

Additionally or alternatively, one or more signaling lines may be provided to synchronize the operation of the transport plane, the transfer device and the laboratory station.

It may, for example, be possible to fill a sample container rack by the transfer device. If the sample container rack is completely filled, the transfer device may signal this condition by a corresponding signaling line to the laboratory station. The laboratory station may then process this sample container rack.

If the container carrier or the sample container comprises a RFID tag, a RFID reader may detect the presence of the container carrier if the container carrier enters a reading distance of the RFID reader. Also an image processing system including a camera may be provided to determine the presence of a container carrier/sample container. The image processing system, the sensors and/or the RFID reader may be part of the transfer device.

According to one embodiment, the transport plane can be fixed to the transfer device and the transfer device can be fixed to the laboratory station. This, for example, can be achieved by screwing, by latching and/or by clamping the items together.

The transfer device may transfer the sample item along at least two axes. Due to the highly flexible transport plane capable of moving the container carriers at various different transfer positions, it can be basically sufficient if the transfer device transfers the sample item along only two axes. These axes may, for example, be the Z axis enabling the transfer in a direction perpendicular to the transport plane, i.e. providing a height movement, and the X- or the Y-axis providing a movement to and/or from the laboratory station.

Due to the flexible transport system, container carriers can be conveyed into a single transfer location per laboratory station for transferring a sample item to the laboratory station. Accordingly, the transfer device can be kept simple and can be reduced to operate along only two axes.

The transfer device may transfer more than one sample item in parallel, thereby increasing the processing performance.

The transport plane may comprise at least one transfer area located adjacent to the at least one transfer device. The transfer area may store a fixed or variable number of container carriers at different positions. The transfer device may, for example, automatically, transfer the sample item between at least one specific transfer location of the transfer area and the laboratory station. The transfer area may provide a dynamic processing queue for a corresponding laboratory station, thereby enabling a flexible load balancing for a specific laboratory station. The dynamic processing queue may get longer if a large number of samples have to be processed by the corresponding laboratory station having a limited processing capacity. The non-processed sample carriers or samples can be queued within the transfer area. The number of locations may be fixed or variable. If the number is variable, the size of the transfer area may be dynamically increased in response to the number of container carriers waiting for processing.

The transfer area may comprise priority areas. The transfer device may be arranged to, for example, automatically, transfer the sample item between at least one specific priority location of the priority area and the laboratory station with priority, i.e. with priority compared with sample items of the conventional transfer location. Priority areas can speed up the handling of emergency samples being distributed between the laboratory stations, thereby reducing the overall processing time of emergency samples significantly compared with systems without prioritization.

The transport plane may comprise at least one buffer area to store container carriers not carrying a sample container. These empty container carriers located in the buffer area may be filled with sample containers comprising samples to be processed. If an empty container carrier having a container carrier ID is filled with a sample container having a sample container ID, a database storing matching container carrier IDs and sample container IDs may be updated. The stored matching between the IDs may be checked, for example, before the corresponding sample is analyzed and/or if the sample container is removed from the transport plane. If the IDs do not match, which may, for example, be caused by manually swapping sample containers, an error may be generated. This may prevent erroneous analyzing results.

The filling or placing of sample containers in corresponding container carriers may be done manually or automatically, for example, by a corresponding transfer device picking sample containers out of a sample container rack comprising a number of sample containers to be processed. The sample container rack may be placed manually within an operating range of the transfer device.

The system may comprise a container carrier conveyor or conveyor belt system functionally coupled to the transport plane, i.e. having a transport gateway to transfer container carriers and/or sample containers between the transport plane and the conveyor. The container carrier conveyor may convey container carriers not being placed on top of the transport plane. The container carrier conveyor may be a conventional transport system, for example, be suited for long distance transportation of the container carriers. The combination of the transport plane and the conveyor provides for a flexible distribution of samples where necessary and a cost effective, rapid distribution over long distances. The electro-magnetic actuators may be controlled such that a speed of a sample container intended to be transferred from the transport plane to the conveyer matches with the linear speed of the conveyer.

The system may comprise at least one RFID reader. Each container carrier can comprise a RFID tag storing a unique ID, thereby making an identification of a specific container carrier easily possible. The system may comprise at least one barcode reader. Each sample container can carry a barcode representing sample identification. The barcode reader may be in the at least one transfer device.

The transfer device may further comprise a camera for image processing. By use of the barcode reader and/or the camera the transfer device can be capable of determining features of the sample items provided for transfer and to use these features in the transfer process. The features may comprise a tube type, a cap type, a fluid level, a sample quality, a sample color, sample identification, and the like.

The transfer device may comprise a pick-and-place device. The pick-and-place device can pick a sample item or a sample container from the transport plane and place the sample item or the sample container in a sample container rack. Additionally or alternatively, the pick-and-place device may pick a sample item or a sample container from a sample container rack and place the sample item or sample container in a container carrier placed on the transport plane.

The pick-and-place device may rotate the sample container to enable a barcode reader, for example, part of the transfer device, to read a barcode attached to the sample container. The pick-and-place device may move a grabber only in a vertical direction (Z) and in one horizontal direction (X or Y).

The transfer device may comprise at least one conveyor, for example, in the form of a conveyor belt having a pusher. The conveyor can move a sample container rack from a pick-and-place device towards a laboratory station and/or move a sample container rack from a laboratory station towards the pick-and-place device. Such a configuration can make it possible to use a pick-and-place device moving only in the vertical direction (and one horizontal direction) since the transport towards the laboratory station can be done by the conveyor.

The transfer device may comprise a sample container rack storage device to store sample container racks. The sample container racks can include a number (for example, about 1 to 128) of sample containers. Such sample container racks can typically be used in laboratory stations operating rack based. The sample container rack may be filled manually or automatically, for example, by a corresponding transfer device.

The sample container rack storage device may store sample container rack trays. Each sample container rack tray can store a plurality, for example, about 2 to 24, of sample container racks.

The sample container rack storage device may comprise a push loading drawer. The push loading drawer can have an open and a closed state. In the open state, the push loading drawer can be filled with sample container racks and/or sample container rack trays. In the closed state, the push loading drawer may supply sample container racks or sample container rack trays if necessary.

The sample container rack storage device may store sample container racks or sample container rack trays in at least one storage level below a transport plane level of the transport plane. The sample container rack storage device can comprise an elevator device. The elevator device can lift a sample container rack or a sample container rack tray from the at least one storage level to the transport plane level. Lowering the storage level below the transport plane level can make it possible to use the space below the transport plane for storing sample container racks or a sample container rack trays.

The transfer device may automatically remove a sample container rack from the sample container rack storage device, sequentially or in parallel take a plurality (corresponding to the capacity of the sample container rack) of sample containers to be transferred from the transport plane and insert them into the sample container rack and provide the sample container rack including the inserted sample containers to the laboratory station. Accordingly, the transfer device may transfer processed sample containers from the transport plane back into sample container racks.

The laboratory system can comprise at least one laboratory station such as, for example, a pre-analytical, an analytical and/or a post-analytical station, and a laboratory sample distribution system. The pre-analytical, analytical and/or a post-analytical stations may comprise at least one of a decapping station, a recapping station, an aliquot station, a centrifugation station, an archiving station, a pipetting station, a sorting station, a tube type identification station, and a sample quality determining station.

The laboratory system may comprise a memory device storing matching pairs of a unique ID corresponding to a container carrier and a container ID carried by the container carrier making it possible to control and track the path of a sample container over the transport plane.

The method of operating a laboratory system can comprise moving a container carrier from a start location to a destination location over the transport plane by the electro-magnetic actuators, transferring a sample item between the destination location and a laboratory station adjacent to the destination location by the transfer device, and performing a pre-analytical, an analytical and/or a post-analytical function by the laboratory station. The start location may be a location on the transport plane which can be intended for importing container carriers into the laboratory system. These imported container carriers can carry sample containers comprising samples intended for an analysis. Further, the start location may be a location on which container carriers can be placed after being served by a station. The destination location may, for example, be located within a transfer area. In other words, a container carrier can travel over the transport plane between laboratory stations needed for the intended analysis. By the transfer device, the sample item can be transferred to the stations. In the case of sample containers, the transfer device may also transport the container back into a container carrier on the transport plane. For this, the same container carrier may be used in which the sample container was located before or a new container carrier may be employed.

The method may further comprise manually or automatically feeding a sample container to the laboratory system, determining laboratory stations needed for processing a sample contained in the sample container, moving the sample container to the determined laboratory stations, and processing the sample container and/or the sample by the determined laboratory stations. The laboratory stations needed for processing may be determined by reading sample information attached to the sample container. The sample information attached to the sample container may be incorporated in form of a barcode attached to the sample container.

The at least one permanent magnet of the container carrier may be ball-shaped, wherein a north pole or a south pole of the ball-shaped permanent magnet can be directed to the transport plane. In other words, an axis extending through the opposite poles of the ball-shaped permanent magnet can be perpendicular to the transport plane. A diameter of the ball-shaped permanent magnet may be approximately 12 mm. The ball-shaped permanent magnet can cause an optimized magnetic field in interaction with the electro-magnetic actuators, for example, compared with a bar magnet, resulting in higher magnetic force components in a lateral movement direction.

The permanent magnet in conjunction with a ferromagnetic core of a currently adjacent non-activated electro-magnetic actuator can cause an unwanted magnetic retention force. The retention force can hinder the desired movement of the container carrier away from the currently adjacent non activated electro-magnetic actuator towards an activated electro-magnetic actuator. Increasing the distance between the permanent magnet and the transport plane, i.e. also increasing the distance between the permanent magnet and the electro-magnetic actuators, can reduce this magnetic retention force. Unfavorably, an increasing distance can also lower a desired magnetic transport force in a lateral movement direction. Therefore, a distance between a center of the at least one permanent magnet and a bottom surface of the container carrier, the bottom surface can be in contact with the transport plane, may be selected within a range of about 5 mm to about 50 mm. The given distance range can provide an optimum between a desired magnetic transport force in movement direction and an unwanted magnetic retention force.

The container carriers may comprise a first permanent magnet arranged in the center of a stand of the container carrier and a second permanent magnet having a ring shape arranged in the stand surrounding the first permanent magnet. This arrangement can provide a high flexibility in causing push and pull magnetic forces, especially if more than one electro-magnetic actuator is activated at a given time. The first and second permanent magnets may have a reverse polarity, i.e. a south pole of the first permanent magnet and a north pole of the second permanent may point to the transport plane, or vice versa. The ring shaped second permanent magnet may constitute a circular area having a diameter that can be less than a distance between axes of electro-magnetic actuators of the transport plane.

The container carriers may comprise a RFID tag storing a unique ID. This can enable matching between a sample container ID, for example, a barcode, and the corresponding container carrier. The unique carrier ID can be read by an optional RFID reader being part of the system and being placed at one or more specific locations within the system.

The RFID tag may comprise a ring shaped antenna arranged in a stand of the container carrier. This antenna arrangement can make it possible to read the RFID tag by a RFID reader antenna below the transport plane. Thus, the transport plane itself and/or areas above the transport plane may be designed free of any disturbing RFID reader antennas.

A stand of the container carrier can have a circular cross section having a diameter of approximately 3.5 cm to 4.5 cm. The circular cross section of the stand can reduce the likelihood of a stand collision of container carriers moving adjacent in different directions. Compared, for example, with quadratic stands, this can reduce the required safety distance between adjacent positions and the requirements on positioning accuracy. Further, the circular stand can improve the self-supporting of the container carrier, for example, can prevent that the containers carrier tilts under normal operating conditions.

The electro-magnetic actuators may comprise a ferromagnetic core guiding and amplifying a magnetic field. The electro-magnetic actuators may have a center finger and four outer fingers, each of the fingers extending perpendicular to the transport plane. Only the center finger may be surrounded by a coil being driven by an actuating current. This arrangement can reduce the number of coils needed for activating the electro-magnetic actuators. The center finger and the outer fingers can interact advantageously by providing push and pull forces, respectively, especially if the container carrier comprises a first permanent magnet arranged in the center of the stand and a second permanent magnet having a ring shape arranged in the stand surrounding the first permanent magnet.

The system may further comprise a container carrier sensing device to sense the presence and/or position of container carriers located on the transport plane. The container carrier sensing device can provide for an optimized tracking of container carriers placed on top of the transport plane.

The container carrier sensing device may be embodied based on infra-red (IR) based reflection light barriers. These light barriers might be arranged in recesses in the transport plane or might be arranged below a transport plane which can at least be partially transparent for the employed light. In the latter case, a closed transport plane can be provided which inter alia can be easier to clean.

The electro-magnetic actuators may be arranged in rows and columns forming a grid or matrix of active transport fields. According to one embodiment, the rows and columns can have either a first grid dimension g1 or a second grid dimension g2, wherein g2=2*g1. Adjacent rows and adjacent columns can have different grid dimensions. The grid dimension can specify a distance between adjacent or consecutive electro-magnetic actuators in a given row or column. In other words, the electro-magnetic actuators can be arranged in the form of a grid or matrix. The grid or matrix can have blank positions representing omitted electro-magnetic actuators. This arrangement can consider that diagonal movements of the container carriers may not be necessary to reach a specific destination on the transport plane, since the specific destination can be reached based on movements along the rows and columns. This arrangement of the electro-magnetic actuators can reduce the number of required electro-magnetic actuators significantly (by, for example, about 33%) compared to having a constant grid dimension. Nevertheless, if a diagonal movement is required, it can be self-evident that the rows and columns may be provided having a constant grid dimension, for example, forming a transport plane being divided in active transport fields with equal dimensions.

The transport plane may be divided into multiple sub-planes. Each sub-plane can have a first outer face, a second outer face, a third outer face and a fourth outer face at which further planes can be arranged in a tiling manner to form a transport plane. This approach can offer the ability to provide transport planes of desired shape. This can be a big advantage to serve the needs an individual laboratory might have due to the laboratory stations present or due to spatial restraints.

The approach to build the transport plane from sub-planes can be combined with the concept of rows having different grid dimensions to reduce the number of needed electro-magnetic actuators. Sub-planes can be employed where along the first and the second outer face the electro-magnetic actuators can be arranged in a first grid dimension g1 and along the third and the fourth outer face the electro-magnetic actuators can be arranged in a second grid dimension g2, wherein g2=2*g1. Multiple sub-planes can be adjacent in a tiling manner to form the transport plane. Adjacent outer faces of different sub-planes can have different grid dimensions.

The system may comprise a magnetizable coupling element to provide a magnetic coupling between adjacent electro-magnetic actuators. Due to the coupling element, the activated electro-magnetic actuator can automatically cause a magnetic field in the adjacent actuators having an inverse polarization. This can automatically provide respective pull and push forces even if only a single electro-magnetic actuator is activated, for example, by a corresponding activating current.

The surface of the container carriers and the surface of the transport plane may be arranged to reduce friction between the surfaces, for example, by coating the container carriers and/or the transport plane.

The system may comprise a cover profile covering the transport plane, especially covering multiple sub-planes forming the transport plane. The cover plane can be fluidtight. The cover plane can simplify the cleaning of the transport plane and can avoid disturbing gaps between adjacent sub-planes, when the transport plane is formed of multiple adjacent sub-planes. Further, the cover profile can mitigate height differences between adjacent sub-planes. The cover profile may be just overlying the transport plane or may be glued to the top surface of the sub planes to stabilize the arrangement and to prevent spacing which would reduce magnetic forces.

A method for the versatile transport of sample containers can be achieved with laboratory sample distribution system comprising a plurality of container carriers. The container carriers can comprise at least one magnetically active device and can carry a sample container. The laboratory sample distribution system can further comprise a transport plane to carry the container carriers and a plurality of electro-magnetic actuators stationary arranged below the transport plane. The electro-magnetic actuators can move a container carrier on top of the transport plane by applying a magnetic force to the container carrier. The method can comprise activating at least one of the electro-magnetic actuators to apply a magnetic force to a container carrier within an operating distance of the at least one activated electro-magnetic actuator. Activating an electro-magnetic actuator can mean that a magnetic field can be generated by the electro-magnetic actuator. Activating may be done by generating a driving current applied to a coil surrounding a ferromagnetic core.

A speed of a container carrier moving across the transport plane may be set by setting a period between a successive activation of adjacent electro-magnetic actuators. If this duration is set shorter, the speed can increase and vice versa. By changing the duration dynamically, a container carrier may be accelerated or slowed down.

The electro-magnetic actuators may be activated in response to a sensed position of the container carrier to be applied with the magnetic force. The electro-magnetic actuators may be activated such that a polarity of the generated magnetic field can depend on a position of the container carrier relative to the electro-magnetic actuator. This can cause position-depended pull and push forces. In a first position range when the container carrier is moving towards the activated electro-magnetic actuator, the pull force may attract the container carrier towards the activated electro-magnetic actuator. In a second position range when the container carrier has traversed the electro-magnetic actuator, the push force may push the container carrier away from the activated electro-magnetic actuator now generating a magnetic field having an opposite polarity. Additionally, the magnetic field strength may be changed in response to the sensed position to provide a steady movement of the container carrier. The electro-magnetic actuators may generate magnetic fields having only a single polarity to simplify the system. In this case, the activated electro-magnetic actuator may generate the pull force in the first position range when the container carrier is moving towards the activated electro-magnetic actuator. In the second position range when the container carrier has traversed the electro-magnetic actuator, the electro-magnetic actuator may be deactivated.

For moving a first container carrier along a first transport path, a first group of electro-magnetic actuators may be activated along the first transport path. For independently and at least partially simultaneously moving, a second container carrier along a second transport path a second group of multiple electro-magnetic actuators may be activated along the second transport path. The term "simultaneously" can mean that during a certain time interval both the first and the second container carrier move. The electro-magnetic actuators of the first or the second group may be activated one after the other along the respective transport path. Alternatively, two or more adjacent electro-magnetic actuators along the respective transport path may be activated at least partially overlapping in time.

A movement of a container carrier placed on a field on top of a first electro-magnetic actuator to an adjacent field on top of a second electro-magnetic actuator may comprise activating the first and the second electro-magnetic actuator and a third electro-magnetic actuator adjacent to the first electro-magnetic actuator and opposite to the second electro-magnetic actuator and part of the same row or column as the first and the second electro-magnetic actuators in a predetermined order.

If the container carriers comprise a first permanent magnet arranged in the center of a stand of the container carrier and a second permanent magnet having a ring shape arranged in the stand surrounding the first permanent magnet, the method may further comprise activating the second electro-magnetic actuator such that a resulting pull-force regarding the second permanent magnet having a ring shape can be generated, and activating the third electro-magnetic actuator such that a resulting push-force regarding the second permanent magnet can be generated; after a predetermined time interval or at a predetermined position of the container carrier, activating the first electro-magnetic actuator such that a resulting pull-force regarding the second permanent magnet can be generated and that a resulting push-force regarding the first permanent magnet can be generated; and after a second predetermined time interval or at a second predetermined position of the container carrier: activating the second electro-magnetic actuator such that a resulting pull-force regarding the second permanent magnet can be generated. A movement between adjacent electro-magnetic actuators can be done in a sequence of three activation patterns regarding three adjacent electro-magnetic actuators. This can lead to a continuous uniform movement with a high positioning accuracy. The first and second time interval or the first and the second position may be determined based on a sensed position of the container carrier provided by the container carrier sensing device.

Figure 1:
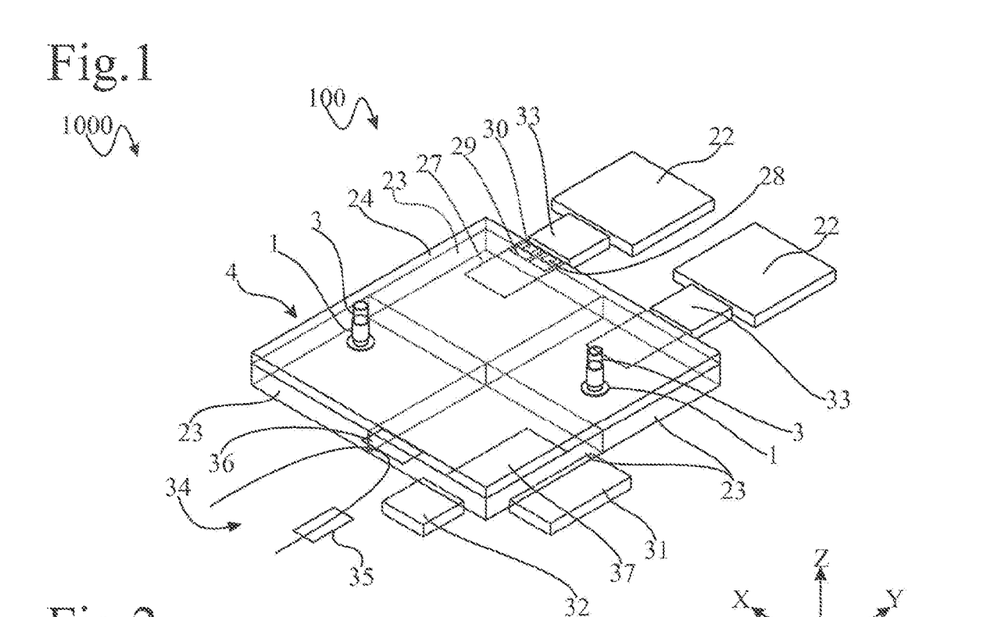
FIG. 1 illustrates a laboratory system comprising a laboratory sample distribution system having a transport plane formed of multiple sub-planes according to an embodiment of the present disclosure.

Referring initially to FIG. 1, FIG. 1 shows a laboratory system 1000 comprising pre-analytical, analytical and post-analytical stations 22 such as, for example, in the form of a decapping station, a recapping station, an aliquot station, a centrifugation station, an archiving station, a pipetting station, a labeling station, a sorting station, a tube type identification station, an analyzer, and a probe quality determining station; and a laboratory sample distribution system 100. FIG. 1 shows only two exemplary laboratory stations 22, nevertheless it is self-evident that more than two laboratory stations may be provided.

The laboratory sample distribution system 100 can be used to distribute samples or specimens such as, for example, blood samples, contained within sample containers 3 between the different laboratory stations 22.

The laboratory sample distribution system 100 can comprise a plurality of container carriers or Single-Tube-Carriers 1 each carrying a corresponding sample container 3 over a transport plane 4. Multiple electro-magnetic actuators 5 (see FIGS. 2 and 3) can be stationary arranged below the transport plane 4. Each of the electro-magnetic actuators 5 can move a container carrier 1 in operating distance of a corresponding electro-magnetic actuator 5 by applying a magnetic force to the container carrier 1.

The system can further comprise a barcode reader 31, a RFID reader 32, transfer devices 33 corresponding to the laboratory stations 22 and a conventional belt-driven container carrier conveyor 34 operationally coupled to the transport plane 4.

The depicted transport plane 4 can be divided into four quadratic sub-planes 23. The sub-planes 23 can be adjacent to one another. The transport plane can be covered by an optional cover profile 24. The cover profile 24 can be fluidtight and can cover gaps and mitigate height differences between adjacent sub-planes 23. The material of the cover profile 24 can provide a low friction coefficient. The cover profile 24 may, for example, be a glass plate or a foil of polyethylene or PTFE (poly-tetra-fluoro-ethylene).

The transfer devices 33 can transfer a sample item between the transport plane 4 and a corresponding laboratory station 22. The sample item may be a container carrier 1 together with a corresponding sample container 3, a sample container 3 including the sample, part of the sample or the complete sample without the corresponding sample container 3.

Each transfer device 22 can transfer the sample item along at least two axes, for example, along the Z-axis and the Y-axis. At least some of the transfer devices 22 may transfer more than one sample item in parallel to speed up the transfer capacity. The transfer devices 22 may be pick-and-place devices, multi-axis robots having a picker, pipettors, and the like.

Usage of the transfer devices can provide that conventional laboratory devices can be employed in conjunction with the transport system without the need to re-design existing laboratory devices or to adapt them specifically to the transport system.

In order to provide processing queues, the transport plane 4 can comprise transfer areas 27 located adjacent to corresponding transfer devices 22. The transfer areas 27 can store in a one- or two-dimensional queue a plurality, for example, about 10 to 20, of container carriers 1. The corresponding transfer device 33 can transfer the sample item between at least one specific transfer location 28 within the transfer area 27 and the corresponding laboratory station 22 and vice versa.

In order to provide optimized processing paths for emergency samples, each transfer area 27 can comprise priority areas 29. The corresponding transfer device 33 can transfer the sample item between a specific priority location 30 within the priority area 29 and the corresponding laboratory station 22 with priority, i.e. prior to those sample items being placed on the non-prioritized transfer-location 28.

In order to handle container carriers not carrying a sample container, the transport plane 4 can comprise a buffer area 37 to store container carriers 3 not carrying a sample container. Alternatively or in addition, a buffer unit for unloaded container carriers may be provided which can be located adjacent the transport plane. The buffer unit may have an in-build transfer mechanism for transferring container carriers from the buffer unit onto the transport plane or a transfer device as described above may be used in between the buffer unit and the transport plane.

Figure 5:
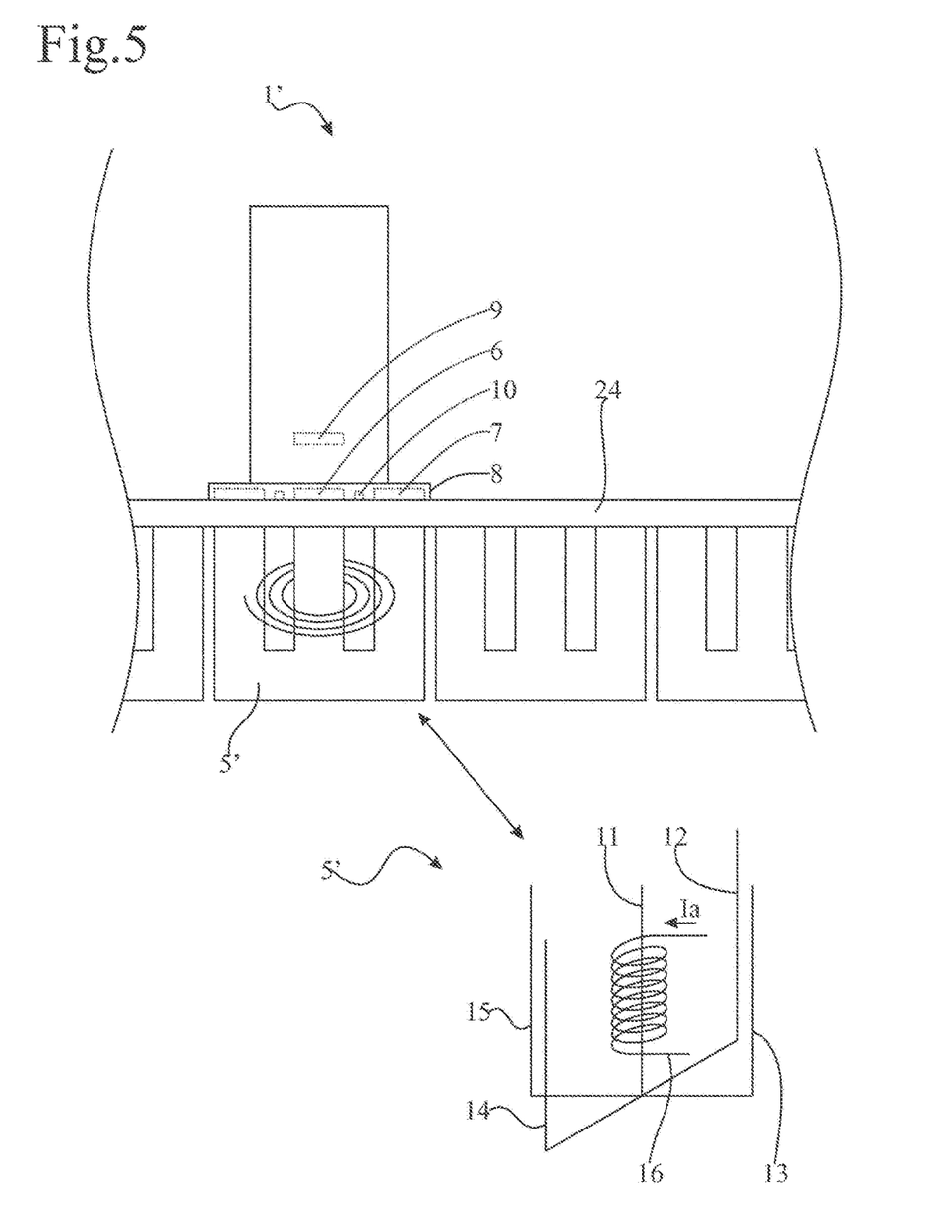
FIG. 5 illustrates a container carrier and a corresponding electro-magnetic actuator according to a second embodiment of the present disclosure.

The RFID reader 32 can be used to interact with RFID tags 9 comprised in each container carrier 1 (see FIG. 5). The barcode reader 31 can read a barcode (not shown) on the sample containers 3 representing sample characteristics. The laboratory system 1000 can comprise a memory device as part of a laboratory system control device (not shown) for storing matching pairs of a unique ID corresponding to a container carrier and a barcode of a sample container carried by the container carrier in order to track sample containers 3 over the processing path.

The conventional belt-driven container carrier conveyor 34 can be functionally coupled by a transport gateway 36 to the transport plane 4. The container carrier conveyor 34 can convey container carriers 3 not being placed on top of the transport plane 4 in corresponding racks 35.

Figure 2:
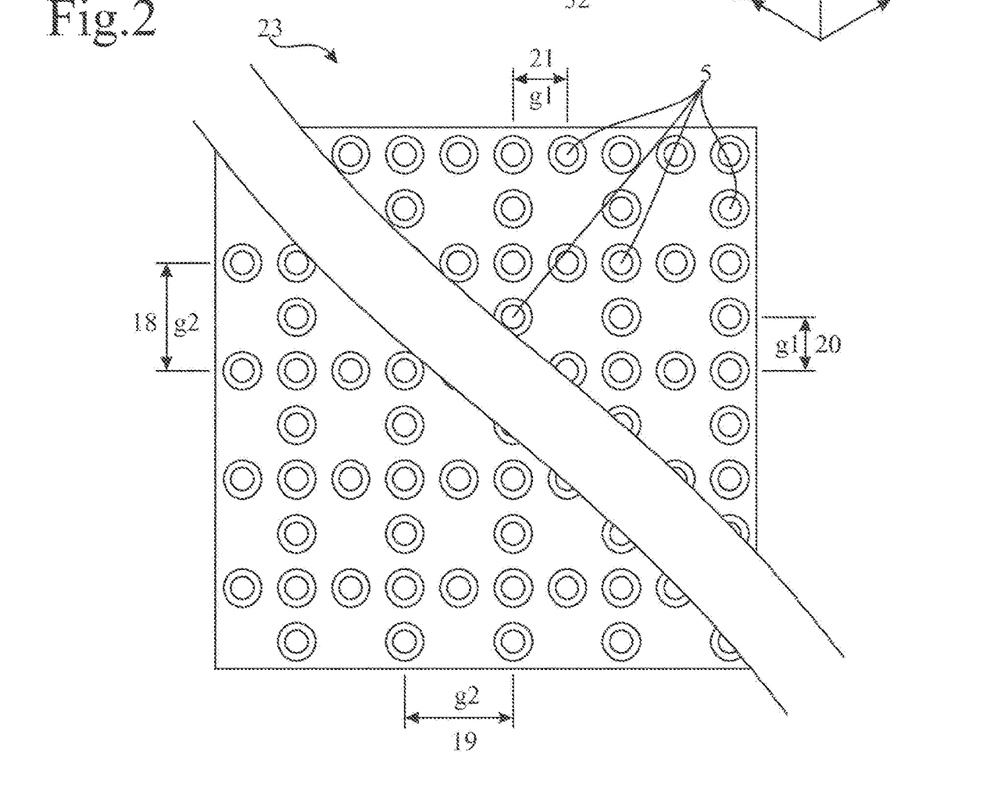
FIG. 2 illustrates a top view on an exemplary sub-plane shown in FIG. 1 according to an embodiment of the present disclosure.

FIG. 2 shows a schematic top view on an exemplary sub-plane 23 of FIG. 1. The sub-plane can have a first outer face 20, a second outer face 21, a third outer face 18 and a fourth outer face 19. Along the first and the second outer face 20 and 21, the electro-magnetic actuators 5 can be arranged in a first grid dimension g1. Along the third and the fourth outer face 18 and 19, the electro-magnetic actuators 5 can be arranged in a second grid dimension g2, wherein g2=2*g1. The grid dimension g1 may, for example, be approximately 20 mm.

The electro-magnetic actuators 5 can be arranged in rows and columns, for example, 16 rows and 16 columns. The rows and columns can have either a first grid dimension g1 or a second grid dimension g2, wherein g2=2*g1 and adjacent rows can have a different grid dimension and adjacent columns can have a different grid dimension. If a position or field on the transport plane has to be accessible as a target destination, a corresponding electro-magnetic actuator can be provided below that target destination. If a specific field or area has not to be accessible, an electro-magnetic actuator may be omitted at that position.

Figure 3:
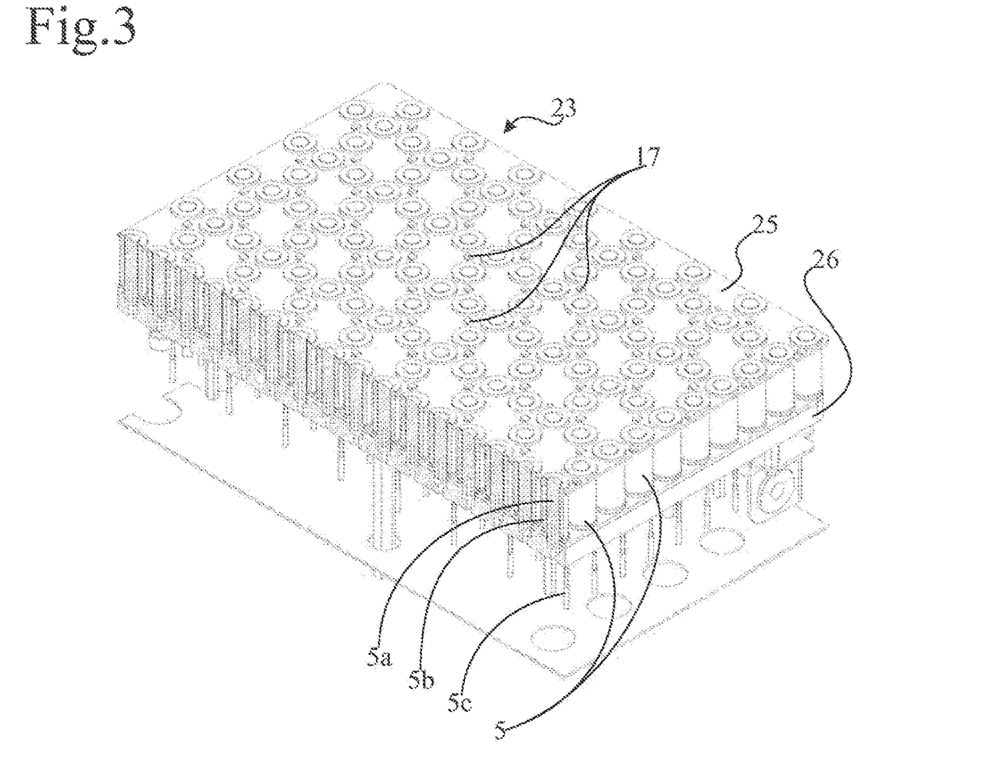
FIG. 3 illustrates a detailed perspective side view of the sub-plane shown in FIG. 2 according to an embodiment of the present disclosure.

FIG. 3 shows a detailed perspective side view of the sub plane 23 shown in FIG. 2. As illustrated, each electro-magnetic actuator 5 can be fixed on a carrier plate 26 and can comprise a ferro-magnetic cylindrical core 5a extending substantially perpendicular to the transport plane 4. A coil 5b can surround the ferro-magnetic cylindrical core 5a. The coil 5b can be applied with an actuating current provided by a driver unit (not shown) over electrical contacts 5c. If driven by an actuating current, each electro-magnetic actuator 5 can generate a magnetic field. When this field interacts with a permanent magnet 2 (see FIG. 4) arranged in the container carrier 1, it can provide a driving force moving the container carrier 1 along the transport plane 4. The ferro-magnetic cylindrical core 5a can bundle and amplify the magnetic field generated by the coil 5b.

In the most simple form, each container carrier 1 may be exposed to a driving force generated by a single activated electro-magnetic actuator 5 proximate to the corresponding container carrier 1 thereby pulling the container carrier 1 towards the activated electro-magnetic actuator 5. Further, it can be possible to superpose push and pull driving forces of multiple electro-magnetic actuators 5 proximate to the corresponding container carrier 1. Further, it can be possible to activate multiple electro-magnetic actuators 5 at the same time to move multiple different container carriers 1 independent of each other along predetermined paths over the transport plane 4.

In order to sense the presence and position of container carriers 1 located on the transport plane 4, a container carrier sensing device can be provided. One embodiment can comprise a printed circuit board 25 having multiple IR based reflection light barriers 17 arranged in a grid on top as shown in FIG. 3. The IR based reflection light barriers 17 can detect container carriers 1 placed on top of a corresponding light barrier 17 since the container carriers 1 can be arranged to reflect IR radiation emitted by the light barriers 17. If no container carrier is present, no reflected IR light can get into the IR sensor of a corresponding light barrier 17.

Figure 4:
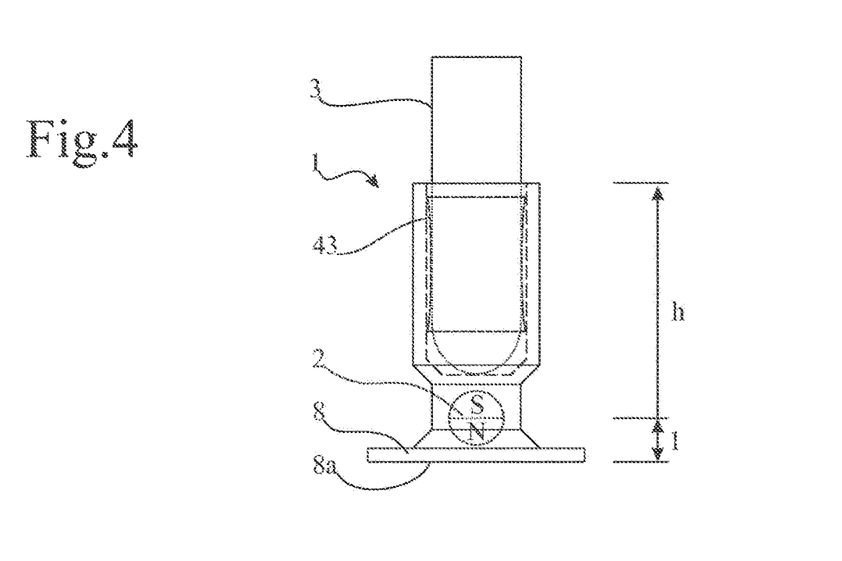
FIG. 4 illustrates a container carrier according to a first embodiment of the present disclosure.

FIG. 4 shows a container carrier 1 according to a first embodiment. The container carrier 1 can comprise a ball-shaped permanent magnet 2. A distance 1 between a center of the at least one permanent magnet 2 and a bottom surface 8a of the container carrier and can lie within a range of about 5 mm to about 50 mm and may be approximately 12 mm. The bottom surface 8a can be in contact with the transport plane 4.

The permanent magnet 2 may be made from hard ferro-magnetic materials. These can include, for example, iron ore (magnetite or lodestone), cobalt and nickel, as well as the rare earth metals. A north pole N of the permanent magnet 2 can be directed towards the transport plane.

A stand 8 of the container carrier can have a circular cross section having a diameter of approximately 3.5 cm to 4.5 cm covering approximately five electro-magnetic actuators 5 if positioned in the center of a cross formed by the five electro-magnetic actuators 5. The electro-magnetic actuator in the center of the cross can be fully covered. The four outer electro-magnetic actuators can be nearly covered by half. Due to this, two carriers moving on adjacent tracks can pass by each other without collision. On the other hand, the footprint can be large enough to provide a smooth transport without much tilting. Accordingly, container carriers may have an optimized circular bottom surface 8a with a radius being about 5 to 30% smaller than the grid distance of the transport plane.

The container carriers may comprise a sample container fixer which may, for example, be incorporated in form of flexible flat spring 43. The flexible flat spring 43 can be arranged at the side wall of the cylindrical opening of the container carrier 3. The flexible flat spring 43 can safely fix the sample container 3 within the container carrier 1 even if the sample container 3 has a smaller diameter than the corresponding opening.

If different sample container types are used, for example, having different form factors, it can even be possible to provide specific container carriers with different inner diameters corresponding to respective sample container types.

FIG. 5 shows a container carrier 1' according to a second embodiment having a different magnet arrangement and a corresponding electro-magnetic actuator 5'. The container carrier 1' can comprise a first permanent magnet 6 arranged in the center of a stand 8 of the container carrier 1' and a second permanent magnet 7 having a ring shape arranged in the stand 8 surrounding the first permanent magnet 6. The permanent magnets 6 and 7 can have a reverse polarity. A north pole of the center permanent magnet 6 and a south pole of the ring shaped permanent magnet 7 can be directed towards the transport plane 4.

Further, the container carrier 1' can comprise a RFID tag 9 storing a unique ID corresponding to a specific container carrier. The RFID tag 9 can comprise a ring shaped antenna 10 which can be arranged in the stand 8 of the container carrier 1' between the first and the second permanent magnet 6 and 7.

The corresponding electro-magnetic actuator 5' can comprise a ferromagnetic core having a center finger 11 and four outer fingers 12, 13, 14, and 15. Each of the fingers can extend perpendicular to the transport plane 4. Only the center finger 11 can be surrounded by a coil 16 driven by an actuating current Ia. This arrangement can reduce the number of coils needed for activating the electro-magnetic actuator 5' compared with the embodiment shown in FIG. 3, wherein the center finger 11 and the outer fingers 12 to 15 interact advantageously by providing push and pull forces, respectively, especially if the container carrier 1' is arranged as shown.

Figure 6:
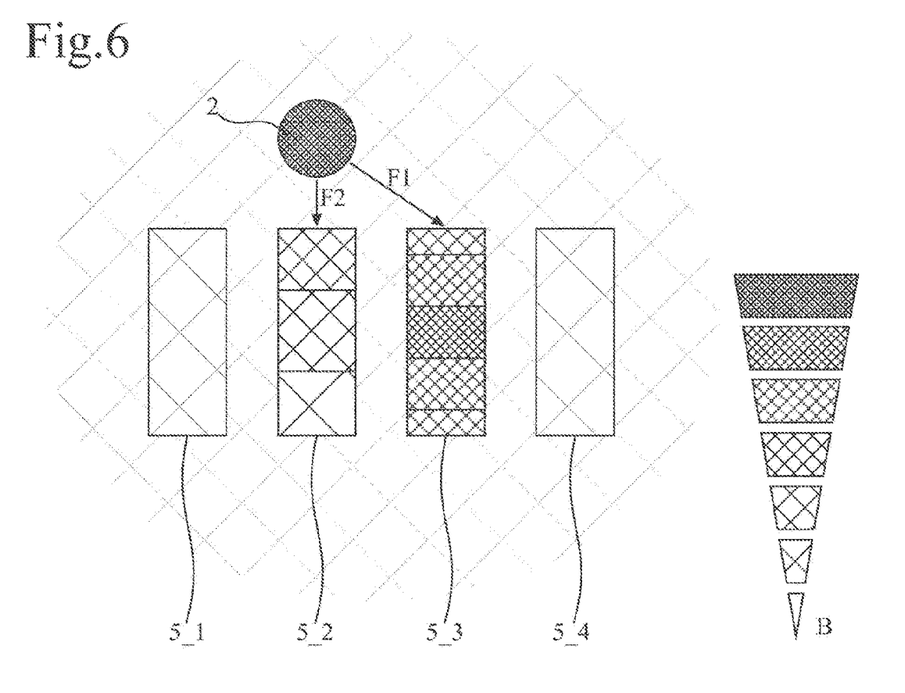
FIG. 6 illustrates a simulated magnetic flux density for the case that a container carrier is positioned on top of an electro-magnetic actuator not being activated and an adjacent electro-magnetic actuator being activated according to an embodiment of the present disclosure.

FIG. 6 schematically shows a simulated magnetic flux density B for the case that a container carrier as depicted in FIG. 4 is positioned on top of an electro-magnetic actuator 5_2 not being activated and an adjacent electro-magnetic actuator 5_3 being activated. Different flux densities B are represented by corresponding hachures. As shown, the ball shaped permanent magnet 2 in conjunction with a ferromagnetic core of the non-activated electro-magnetic actuator 5_2 can cause an unwanted magnetic retention force F2 pulling the permanent magnet 2 towards the ferromagnetic core of the non-activated electro-magnetic actuator 5_2, thereby causing an unwanted force-component in opposite direction of the desired movement and additionally increasing friction between the corresponding surfaces of the transport plane and the stand. The activated electro-magnetic actuator 5_3 can generate a force F1.

In order to reduce these unwanted effects, it can be possible to generate an opposing magnetic field by reversely activating the electro-magnetic actuator 5_2 pushing the container carrier thereby reducing friction. Alternatively or additionally, it can be possible to choose an optimized distance between the permanent magnet 2 and the transport plane, see also the description regarding FIG. 4.

Nevertheless, the magnetic forces in a desired movement direction using a ball-shaped permanent magnet 2 can be higher compared to a bar magnet. A bar magnet bundles the magnetic field in one direction such that the lateral field density is low. Accordingly, the lateral forces which are needed for a lateral transport can be relatively low while the unwanted retention forces can be comparatively high. In the case of a ball shaped magnet, the magnetic field can be less bundled and the lateral field density can be similar to the field density in direction of the transport plane. Accordingly, higher lateral forces can be generated and unwanted retention forces can be lower.

Figure 7:
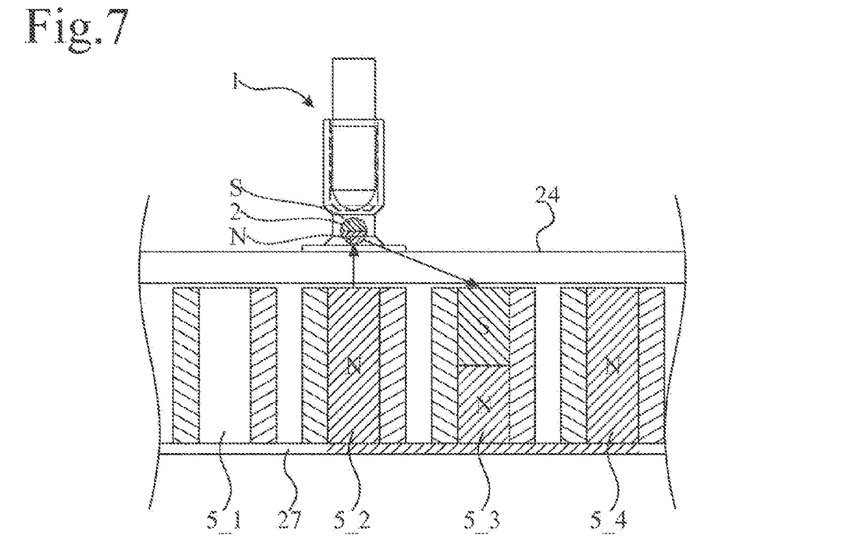
FIG. 7 illustrates a side view of an embodiment of a sub-plane comprising a magnetizable coupling element providing a magnetic coupling between adjacent electro-magnetic actuators according to an embodiment of the present disclosure.

FIG. 7 shows a side view of an embodiment of a sub-plane comprising a magnetizable coupling element 27 providing a magnetic coupling between adjacent electro-magnetic actuators 5. As shown, only the electro-magnetic actuator 5_3 can be activated by driving the corresponding coil with a driving current and can cause a magnetic flow guided by the coupling element 27 and extending in the ferromagnetic cores of the non-activated electro-magnetic actuators 5_2 and 5_3. As a result, a magnetic push force can be generated by the electro-magnetic actuator 5_2 in interaction with the permanent magnet 2 reducing friction and superimposing in the desired direction with a pull force generated by the activated electro-magnetic actuators 5_3.

Figure 8:
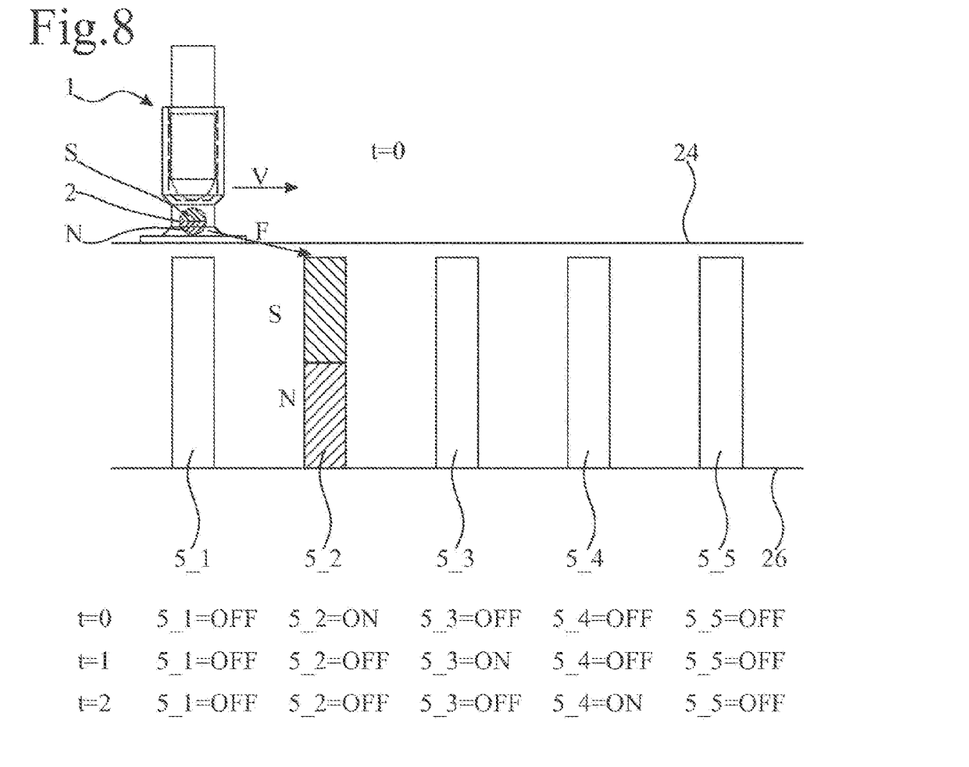
FIG. 8 illustrates a movement of a container carrier and an activation order of corresponding electro-magnetic actuators according to a first embodiment of the present disclosure.

FIG. 8 shows a movement of a container carrier 1 and an activation order of corresponding electro-magnetic actuators 5_1 to 5_5 according to a first embodiment. As shown, at time t=0 only the electro-magnetic actuator 5_2 can be activated such that it can generate a pull force moving the container carrier 1 in the shown direction.

At time t=1, the container carrier 1 has moved such that it can reside on top of the electro-magnetic actuator 5_2, what, for example, can be sensed by the container carrier sensing device. In order to continue the movement, electro-magnetic actuator 5_2 can be deactivated and electro-magnetic actuator 5_3 can be activated, thereby pulling the container carrier 1 forward.

At time t=2, the container carrier 1 has moved such that it can reside on top of the electro-magnetic actuator 5_3. In order to continue the movement, electro-magnetic actuator 5_3 can be deactivated and electro-magnetic actuator 5_4 can be activated, thereby pulling the container carrier 1 forward.

The above steps can be repeated as long as a movement is desired. Concluding, a group of multiple electro-magnetic actuators 5_1 to 5_5 along a transport path can be sequentially activate, to move the container carrier 1 along the first transport path.

Since the electro-magnetic actuators 5 can be activated independently, it can be possible to independently and simultaneously move a plurality of different container carriers 1 along different paths wherein self-evidently collisions have to be avoided.

Figure 9:
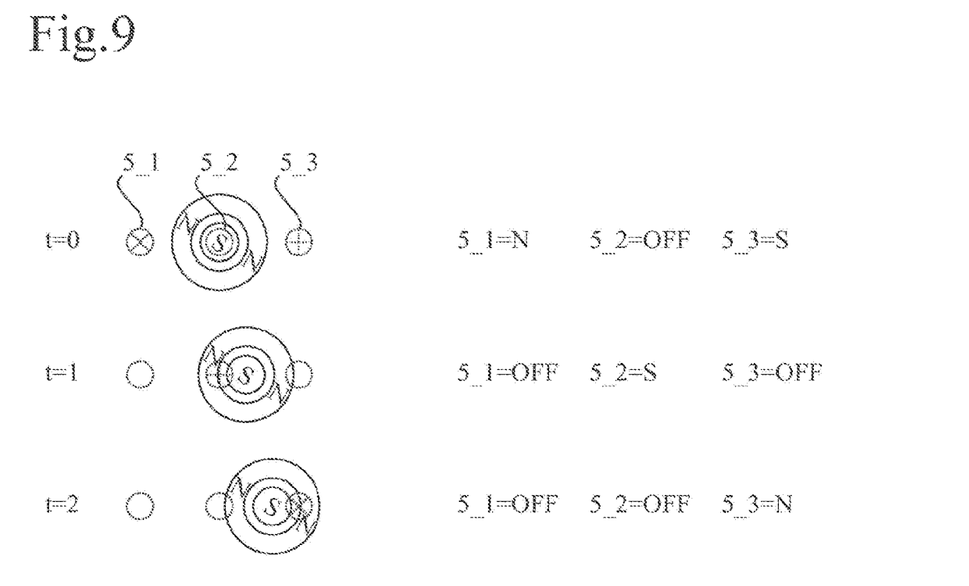
FIG. 9 illustrates a movement of a container carrier and an activation order of corresponding electro-magnetic actuators according to a second embodiment of the present disclosure.

FIG. 9 shows a movement of a container carrier 1' and an activation order of corresponding electro-magnetic actuators 5_1 to 5_3 according to a second embodiment. FIG. 5 shows the container carrier 1' in more detail. In the shown embodiment, a movement of the container carrier 1' placed on a first electro-magnetic actuator 5_2 to an adjacent second electro-magnetic actuator 5_3 can comprise activating the first and the second electro-magnetic actuators 5_2 and 5_3 and a third electro-magnetic actuator 5_1 adjacent to the first electro-magnetic actuator 5_2 in a specific order and polarity. The electro-magnetic actuators 5_1 to 5_3 can be part of the same row or column and can be activated generating a south-pole (S) or a north-pole (N) pointing towards the container carrier 1'.

In a first step at t=0, the second electro-magnetic actuator 5_3 can be activated such that a resulting pull-force regarding the second permanent magnet 7 having a ring shape can be generated and the third electro-magnetic actuator 5_1 can be activated such that a resulting push-force regarding the second permanent magnet 7 can be generated.

After the container carrier 1' reaches a first predetermined position at time t=1, what, for example, can be sensed by the container carrier sensing device, the second and third electro-magnetic actuators 5_1 and 5_3 can be deactivated and the first electro-magnetic actuator 5_2 can be activated such that a resulting pull-force regarding the second permanent magnet 7 can be generated and that a resulting push-force regarding the first permanent magnet 6 can be generated.

After the container carrier 1' reaches a second predetermined position at time t=2, the first and the third electro-magnetic actuators 5_1 and 5_2 can be deactivated and the second electro-magnetic actuator 5_3 can be activated such that a resulting pull-force regarding the second permanent magnet 7 can be generated.

In one embodiment, a movement between adjacent electro-magnetic actuators 5_2 and 5_3 can be performed in a sequence of three activation patterns regarding three adjacent electro-magnetic actuators 5_1 to 5_3. This can lead to a continuous uniform smooth movement with a high positioning accuracy.

Figure 10:
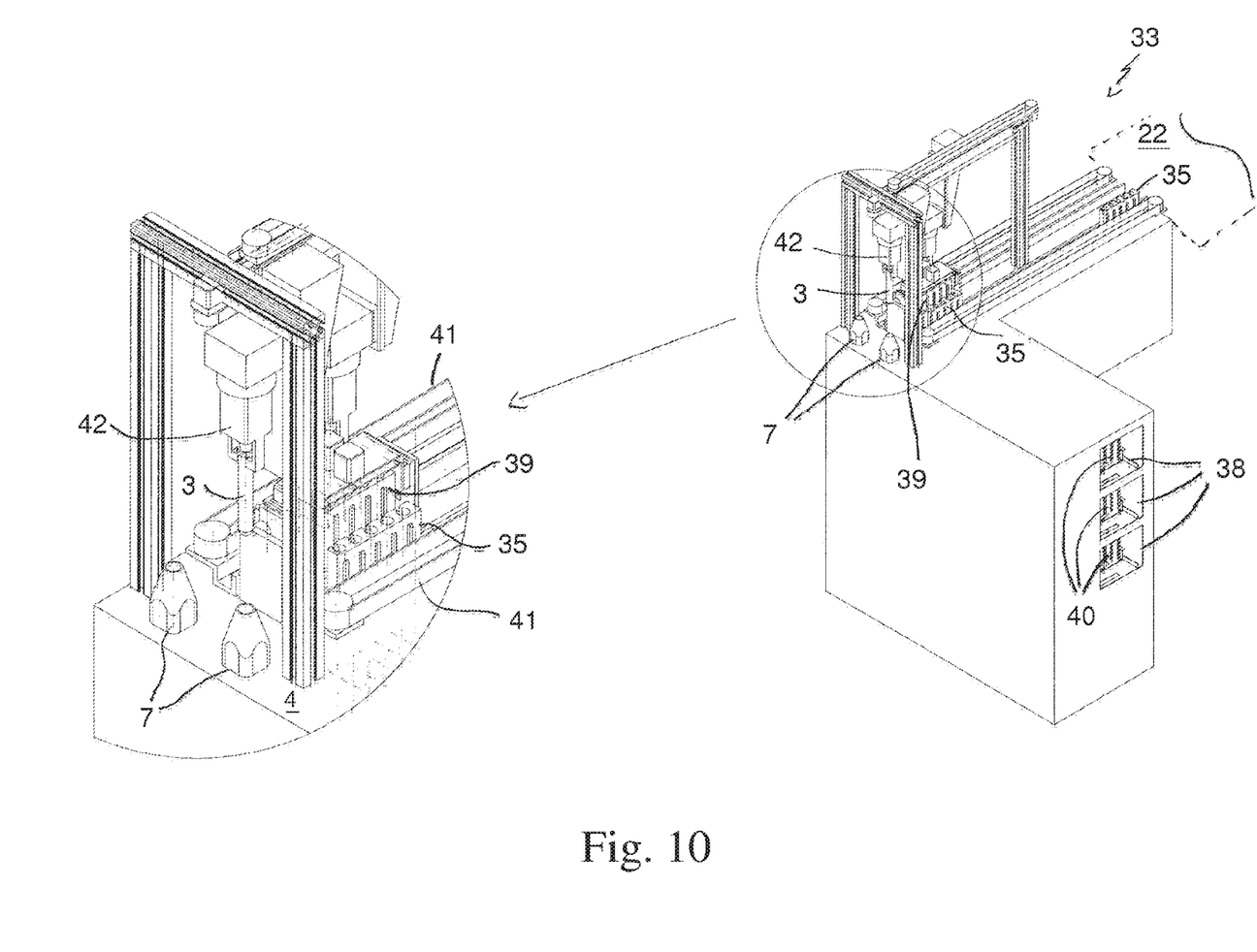
FIG. 10 illustrates a transfer device according to an embodiment of the present disclosure.

FIG. 10 shows a transfer device 33. The transfer device 33 may be arranged adjacent to or partially on top of the transport plane 4 (partially overlapping) and adjacent to a laboratory station 22 (see also FIG. 1). The transfer device 33 can comprise a pick-and-place device 42 movable in a vertical direction (Z direction) and a horizontal direction (X direction and/or Y direction). Further, the transfer device 33 may rotate the sample container 3 along a vertical axis. The transfer device 33 may further pick or grab the sample container 3 only on a sample container body avoiding picking a sample container cap.

The pick-and-place device 42 can pick a sample container 3 from a container carrier 1 placed on the transport plane 4 and can place the sample container 3 in a sample container rack 35 in a formatting operation. In a reformatting operation, the pick-and-place device 42 can pick a sample container 3 from a sample container rack 35 and can place the sample container 3 in an empty container carrier 1 placed on the transport plane 4.

The transfer device 33 can comprise a first and a second conveyor belt 41 to move a sample container rack 35 from a formatting position below the pick-and-place device 42 towards a laboratory station 22 and to move the sample container rack 35 from the laboratory station 22 towards a reformatting position under the pick-and-place device 42.

The transfer device 33 can comprise a sample container rack storage device 38 to store sample container racks 35 in sample container rack trays 40.

The sample container rack storage device 38 can comprise a push loading drawer. The push loading drawer can have an open and a closed state. In the open state, the push loading drawer can be filled with sample container rack trays 40. The sample container rack storage device 38 can store sample container rack trays 40 in three different storage levels below a transport plane level of the transport plane 4. The sample container rack storage device 38 can comprise an elevator device 39. The elevator device 39 can lift a sample container rack 35 from one of the storage levels to the transport plane level.

In the closed state, the push loading drawer can supply sample container rack trays to the elevator device 39. The elevator device 39 can sequentially remove sample container racks 35 from the sample container rack tray and can sequentially lift the sample container racks 35 to the transport plane level.

Concluding, the transfer device 33 can remove a sample container rack 35 from the sample container rack storage device 38, can (sequentially) take a plurality of sample containers 3 to be transferred from the transport plane 4 and can insert them into the sample container rack 35. After the sample container rack 35 is filled, the sample container rack 35 including the inserted sample containers can be transferred to the laboratory station 22 by the first conveyor belt 41.

After being processed, the laboratory station can output the sample container rack 35. The sample container rack 35 can then be transferred to the pick-and-place device 42 by the second conveyor belt 41.

Finally, the pick-and-place device 42 can transfer the sample containers 3 back into corresponding container carriers 1 placed under the pick-and-place device 42 on top of the transport plane 4.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

We claim:

1. A laboratory sample distribution system, the laboratory sample distribution system comprising:
   a plurality of container carriers, each container carrier having a sample container containing a sample, wherein each container carrier comprises at least one magnetically active device;
   a transport plane to carry the plurality of container carriers;
   a plurality of electro-magnetic actuators stationary arranged below the transport plane, wherein the plurality of electro-magnetic actuators moves a container carrier on top of the transport plane by applying a magnetic force to the container carrier and wherein the plurality of electro-magnetic actuators moves the container carrier from a start location to a destination location; and
   at least one transfer device arranged to transfer a sample item between a transfer location on the transport plane and a laboratory station,
   wherein the transport plane comprises at least one transfer area located adjacent to the at least one transfer device, wherein the transfer location is located inside the transfer area, wherein a size of the transfer area is dynamically changed in response to a number of container carriers waiting for processing by the laboratory station.

2. The laboratory sample distribution system according to claim 1, further comprising,
 a container carrier conveyor functionally coupled to the transport plane, the container carrier conveyor being arranged to convey container carriers not placed on top of the transport plane.

3. The laboratory sample distribution system according to claim 2, wherein the container carrier conveyor is belt-driven.

4. The laboratory sample distribution system according to claim 1, further comprising,
 a container carrier sensing device to sense the presence and/or position of container carriers on the transport plane.

5. The laboratory sample distribution system according to claim 1, wherein the at least one transfer device comprises a sample container rack storage device to store sample container racks.

6. The laboratory sample distribution system according to claim 1, wherein non-processed sample carriers are queued within the transfer area.

7. A laboratory sample distribution system, the laboratory sample distribution system comprising:
 a plurality of container carriers, each container carrier having a sample container containing a sample, wherein each container carrier comprises at least one magnetically active device;
 a transport plane to carry the plurality of container carriers;
 a plurality of electro-magnetic actuators stationary arranged below the transport plane, wherein the plurality of electro-magnetic actuators moves a container carrier on top of the transport plane by applying a magnetic force to the container carrier and wherein the plurality of electro-magnetic actuators moves the container carrier from a start location to a destination location; and
 at least one transfer device arranged to transfer a sample container carried by a container carrier on the transport plane to a sample container rack used by a laboratory station in a formatting operation and/or to transfer a sample container from a sample container rack used by the laboratory station to a container carrier on the transport plane in a reformatting operation, wherein the at least one transport device comprises a sensor for determining a rack format of the sample container rack, wherein the transfer device is adapted to perform the formatting operation and/or the reformatting operation rack format specific.

8. The laboratory sample distribution system according to claim 7, wherein the at least one transfer device is a pick-and-place device.

9. The laboratory sample distribution system according to claim 7, wherein the at least one transfer device is a multi-axis robot.

10. The laboratory sample distribution system according to claim 7, wherein the at least one transfer device is a pick-and-place device.

11. The laboratory sample distribution system according to claim 7, wherein the at least one transfer device is a picker.

12. The laboratory sample distribution system according to claim 7, wherein the at least one transfer device is a pipettor.

13. The laboratory sample distribution system according to claim 7, wherein the rack format of the sample container rack corresponds to a specific laboratory station.

* * * * *